United States Patent
Bader et al.

(10) Patent No.: US 6,288,121 B1
(45) Date of Patent: Sep. 11, 2001

(54) NIMESULIDE TOPICAL FORMULATIONS IN THE FORM OF LIQUID CRYSTALS

(75) Inventors: Stefano Bader; Enrique Hausermann; Tiziana Monti, all of Milan (IT)

(73) Assignee: Helsinn Healthcare S.A., Pazzallo-Lugano (CH)

( * ) Notice: Subject to any disclaimer, the term of this patent is extended or adjusted under 35 U.S.C. 154(b) by 0 days.

(21) Appl. No.: 09/355,734

(22) PCT Filed: Feb. 17, 1998

(86) PCT No.: PCT/EP98/00896

§ 371 Date: Aug. 4, 1999

§ 102(e) Date: Aug. 4, 1999

(87) PCT Pub. No.: WO98/37868

PCT Pub. Date: Sep. 3, 1998

(30) Foreign Application Priority Data

Feb. 25, 1997 (IT) ............................................. MI97A0407

(51) Int. Cl.[7] .......................... A61K 31/18; A61K 9/107; A61K 9/113
(52) U.S. Cl. .......................... 514/605; 514/604; 514/844; 514/937; 514/938; 424/401
(58) Field of Search ............................ 424/401; 514/604, 514/844, 605, 937, 938

(56) References Cited

U.S. PATENT DOCUMENTS

| 5,283,261 | * | 2/1994 | Drago | 514/605 |
| 5,688,829 | * | 11/1997 | Jain et al. | 514/605 |
| 5,716,609 | * | 2/1998 | Jain et al. | 424/78.05 |
| 5,837,735 | * | 11/1998 | Miyata et al. | 514/605 |
| 5,942,216 | * | 8/1999 | Herb et al. | 424/70.28 |
| 6,017,932 | * | 1/2000 | Singh et al. | 514/321 |
| 6,136,804 | * | 11/2000 | Nichtberger | 514/605 |
| 6,194,462 | * | 2/2001 | Giorgetti | 514/605 |

FOREIGN PATENT DOCUMENTS

| 43 20 119 | 12/1994 | (DE) . |
| 0 087 062 | 8/1983 | (EP) . |
| 0 782 855 | 7/1997 | (EP) . |
| WO 96/11002 | 4/1996 | (WO) . |

* cited by examiner

*Primary Examiner*—Diana Dudash
*Assistant Examiner*—Shahnam Sharareh
(74) *Attorney, Agent, or Firm*—Young & Thompson

(57) ABSTRACT

Nimesulide topical formulations are provided in the form of liquid crystals. The emulsifier cetylstearyl glycoside is used, and constituents of the lipid phase such as caprylic/capric triglycerides and jojoba oil, consistence factors such as cetylstearyl alcohol. Also disclosed is a process for the preparation thereof. The formulations have advantages such as higher stability, better release and absorption of nimesulide, and a higher bioavailability of the active ingredient.

13 Claims, No Drawings

NIMESULIDE TOPICAL FORMULATIONS IN THE FORM OF LIQUID CRYSTALS

BACKGROUND OF THE INVENTION

1. Field of the Invention

2. Description of the Related Art

The present invention relates to nimesulide topical formulations in the form of liquid crystals.

Nimesulide is a known antiinflammatory agent whose therapeutical efficacy has been proved for some time, but which has the drawback of having unfavourable chemical-physical characteristics; the main obstacle to the use of nimesulide in topical formulations is in fact its insolubility in water and, on the other hand, its poor solubility in the solvents/raw materials usually employed in such formulations.

Some formulations of nimesulide for the external use are described in WO 96/11002; said formulations consist in dispersions of particles of the active ingredient throughout a component which, in the case of creams, comprises a hydorphilic polymer, and oily substance, a surfactant agent, a basic substance and water.

The application does not mention any possible use of liquid crystals for nimesulide topical formulations.

SUMMARY OF THE INVENTION

It has now been found that the emulsions containing liquid crystals, which are the object of the present invention, can be successfully used in nimesulide formulations for the topical use; liquid crystals present at the oil/water interface exert in fact a double effect in that they stabilize the emulsified system and control the release mechanism of the active ingredient, and therefore its bioavailability, thanks to the formation of a network system throughout which the active ingredient is homgeneously dispersed, thus involving unquestionable advantages compared with the conventional formulations containing water-in-oil (W/O) or oil-in-water (O/W) emulsions.

For the formulations of the present invention cetylstearyl glycoside has been used as a non ionic oil in water (O/W) emulsifier, which, in the presence of a suitable aqueous phase, produces gel-structures by formation of liquid crystals. Cetylstearyl glycoside has safety and dermal tolerance characteristics ascribable to the natural origin of the compound itself; its hydrophilic portion derives, in fact, from the strong hydrolysis of starch and its lipophilic portion results from the hydrogenation of fatty acids derivatives of vegetable lipids. Cetylstearyl glycoside can be used at a concentration ranging from 3% to 10% by weight, preferably from 3% to 5%.

The lipid phase of the emulsion consists of a caprylic/capric triglyceride, having a high carrier ability, thus giving the system sostantivity and emollient properties; caprylic/capric triglyceride can be used at a concentration ranging from 2% to 15% by weight, preferably from 2% to 6%.

Moreover, the lipid phase preferably contains a liquid natural wax, namely the jojoba oil, which, besides enhancing nimesulide dispersion capability, provides very good properties of smoothness, flowability, emollient properties, pleasantness and agreeableness of use. The jojoba oil can be used at a concentration ranging from 1% to 15% by weight, preferably from 3% to 7%.

The emulsion also comprises as a "consistence factor", cetylstearyl alcohol, which supplements the action of the cetylstearyl glycoside, due to the affinity between the two alkyl cetylstearyl chains, and contributing to the formation of the crystalline structure of the emulsion.

Cetylstearyl alcohol can be used at a concentration ranging from 2% to 10% by weight, preferably from 2% to 5%.

The formulation of the present invention can also contain emollients/humectants, such as cetyl ester 1–15% by weight, cholesterol 0.3–0.5% by weight, glycerin 1–30% by weight, isopropyl myristate 1–10% by weight, isopropyl palmitate 0.05–5,5% by weight, lecithin 1–20% by weight, lanolin alcohols 0.5–15% by weight, vaseline 4–95% by weight, soy lipids 1–20% by weight, anti-microbial preservatives, such as parabens mixtures, and chemical preservative, for example antioxidants such as tocopherol and lecithin, dermal absorption enhancers, such as propylene glycol 5–50% by weight, 2-pyrrolidone 0.1–10% by weight, pyrrolidone derivatives.

The amount of water in the formulations ranges from 40% to 95% by weight, whereas pH is preferably kept at about 5.5, for example by addition of citric acid, so as to warrant the chemical-physical stability of nimesulide.

Nimesulide can be dispersed in a wide range of concentrations, preferably from 0 to 5% by weight.

The formulations based on liquid crystals of the invention have the following advantages:

improvement in the chemical-physical stability of the emulsion;

homogeneous distribution of the active ingredient in the crystalline structure;

control of the release and absorption of nimesulide;

increase in nimesulide bioavailability;

high compliance by the user.

Said formulations can be prepared by means of a process comprising:

hot preparation of the emulsion containing the two hydrophilic and lipophilic phases and the consistence factors;

separated preparation of the phase containing the active ingredient nimesulide optionally jojoba oil, caprylic/capric triglyceride and optional preservatives;

hot mixing of the two phases from the above steps, and subsequent cooling;

control and adjustment of pH, preferably with citric acid.

The compositions of the invention proved to be well tolerated in animals.

The efficacy of the compositions of the invention has been tested using well-known pharmacological tests.

The following examples further illustrate the invention.

| Phase | Ingredient | % w/w |
|---|---|---|
| Phase A | Purified water | q.s. |
|  | Glycerin | 3.00 |
| Phase B | Cetylstearyl glycoside | 5.00 |
|  | Cetyl alcohol | 2.00 |
|  | jojoba oil | 2.00 |
|  | Caprylic and capric triglyceride | 1.20 |
| Phase C | jojoba oil | 3.00 |
|  | Caprylic and capric triglyceride | 1.80 |
|  | Nimesulide | — |
|  | Parabens in phenoxyethanol | 1.00 |

-continued

| Phase | Ingredient | % w/w |
|---|---|---|
| | Tocopherol-Ascorbyl palmitate soy lecithin-citric acid | 0.01 |
| Phase D | Citric acid 5% sol. | q.s. |

The formulation was prepared at four nimesulide concentrations, i.e., 2%, 3%, 4%, 5% w/w, each concentration in 3 different 6 kg batches.

For the preparation, a Mambretti 25 kg turbodiffuser with cooling/heating water jacket, turbine, blades and vacuum was used.

The A and C phases were mixed separately in a blade mixer, with heating.

A mixture of methyl, ethyl and propyl p-hydroxybenzoates solubilized in phenoxyethanol and propylene glycol was used as preservative.

| | % w/w |
|---|---|
| Water | 77.68 |
| Cetylstearyl glycoside | 5.00 |
| Jojoba esters | 5.00 |
| Caprylic/capric triglyceride | 3.00 |
| Glycerin | 3.00 |
| Cetyl alcohol | 2.00 |
| Nimesulide | 3.00 |
| Phenoxyethanol and methyl, ethyl, propyl parabens | 1.00 |
| Perfluoropolymethylisopropyl ether | 0.30 |
| Tocopherol-ascorbyl palmitate-lecithin-citric acid | 0.01 |

| Chemical-physical-characteristics | At preparation | After 45 days at room temp. | After 45 days at temp. = 40° C. |
|---|---|---|---|
| Aspect | Emulsion compact slightly yellowish | Emulsion compact slightly yellowish | Emulsion compact slightly yellowish |
| pH | 5.13 | 5.00 | 4.92 |

No traces of separation or decrease in viscosity were observed.

| | % w/w |
|---|---|
| Water | 77.98 |
| Cetylstearyl glycoside | 5.00 |
| Jojoba esters | 5.00 |
| Caprylic/capric triglyceride | 3.00 |
| Glycerin | 3.00 |
| Cetyl alcohol | 2.00 |
| Nimesulide | 3.00 |
| Phenoxyethanol and methyl, ethyl, propyl parabens | 1.00 |
| Tocopherol-ascorbyl palmitate-lecithin-citric acid | 0.01 |
| Citric acid 5% sol. | 0.0066 |

| Chemical-physical-characteristics | At preparation | After 45 days at room temp. | After 45 days at temp. = 40° C. |
|---|---|---|---|
| Aspect | Emulsion compact slightly yellowish | Emulsion compact slightly yellowish | Emulsion compact slightly yellowish |
| pH | 5.08 | 5.02 | 4.90 |

No traces of separation or decrease in viscosity were observed.

What is claimed is:

1. A nimesulide composition for topical administration, said composition comprising nimesulide dispersed in a liquid crystal-containing emulsion comprising a lipid phase containing caprylic and/or capric triglycerides, an aqueous phase, cetylstearyl glycoside and cetylstearyl alcohol, wherein said cetylstearyl glycoside causes formation of liquid crystals at an oil/aqueous interface of said lipid phase and said aqueous phase, and wherein said lipid phase optionally contains jojoba oil.

2. The composition according to claim 1, wherein said triglycerides of the lipid phase are present at a concentration ranging form 2% to 15% by weight.

3. The composition according to claim 2 in which said concentration ranges from 2% to 6% by weight.

4. The composition according to claim 1, wherein the jojoba oil is present at a concentration ranging from 1% to 15% by weight.

5. The composition according to claim 1, wherein the cetylstearyl glycoside is present at a concentration ranging from 3% to 10% by weight.

6. The composition according to claim 5 in which said concentration ranges from 3% to 5% by weight.

7. The composition according to claim 1, wherein cetylstearyl alcohol is present at a concentration ranging from 2% to 10% by weight.

8. The composition according to claim 7 in which said concentration ranges from 2% to 5% by weight.

9. The composition according to claim 1, further comprising additives selected from emollients, humectants, absorption enhancers, preservatives.

10. The composition according to claim 9 in which the wetting agent is glycerin.

11. The composition according to claim 9 in which the preservatives are mixtures of parabens, tocopherol and lecithin.

12. The composition according to claim 1 in which the active ingredient nimesulide is present at a concentration up to 5% by weight.

13. A process for preparing the composition of claim 1, which comprises:

preparing an emulsion containing two hydrophilic phases and a lipophilic phase and cetylstearyl glycoside;

separately preparing a phase containing nimesulide, caprylic/capric triglycerides and optional preservatives, and optional jojoba oil;

mixing the phases from the above steps; and adjusting pH of the resulting emulsion.

* * * * *